US007803146B2

(12) United States Patent
Wada et al.

(10) Patent No.: US 7,803,146 B2
(45) Date of Patent: Sep. 28, 2010

(54) SWEAT-ABSORBENT SHEET AND PROCESS FOR MAKING THE SAME

(75) Inventors: Mitsuhiro Wada, Kagawa-ken (JP); Akiko Tange, Kagawa-ken (JP); Kiyoshi Miyazawa, Kagawa-ken (JP); Chieko Toyooka, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 918 days.

(21) Appl. No.: 11/559,121

(22) Filed: Nov. 13, 2006

(65) Prior Publication Data

US 2007/0149933 A1 Jun. 28, 2007

(30) Foreign Application Priority Data

Dec. 28, 2005 (JP) ............................ 2005-380298
Apr. 12, 2006 (JP) ............................ 2006-109897

(51) Int. Cl.
*A61F 13/15* (2006.01)

(52) U.S. Cl. .............................. 604/385.101; 604/358; 604/369; 604/381; 604/379; 604/380

(58) Field of Classification Search ................. 604/358, 604/369, 381, 385.101, 379, 380.381
See application file for complete search history.

(56) References Cited

U.S. PATENT DOCUMENTS 4,530,873 A * 7/1985 Okada ......................... 442/79
2005/0075027 A1* 4/2005 Etchells et al. .............. 442/205

FOREIGN PATENT DOCUMENTS

| | | |
|---|---|---|
| JP | 10-114004 | 5/1998 |
| JP | 2000-189454 | 7/2000 |
| JP | 2001-299811 | 10/2001 |
| JP | 2002-153507 | 5/2002 |
| JP | 2003-089957 | 3/2003 |
| JP | 2003-342862 | 12/2003 |
| JP | 2004-358099 | 12/2004 |

* cited by examiner

*Primary Examiner*—Jacqueline F. Stephens
(74) *Attorney, Agent, or Firm*—Lowe Hauptman Ham & Berner, LLP

(57) ABSTRACT

A sweat-absorbent sheet includes a first surface layer, a second surface layer lying on the opposite side of the first surface layer and an intermediate layer sandwiched between these two layers. Each of the first and second surface layers comprises a mixture layer of first and second hydrophobic fibers made of thermoplastic synthetic resin as main constituent and first and second hydrophilic fibers. The intermediate layer comprises third hydrophilic fibers extending into at least one of the first and second hydrophobic fibers. The first and second hydrophobic fibers are bonded to the crimped to hydrophobic composite fibers mixed in the respective layers. The first, second and third hydrophilic fibers are impregnated with antibacterial or bactericidal medicinal ingredient and such medicinal ingredient is left behind on these hydrophilic fibers after these hydrophilic fibers have been dried.

10 Claims, 3 Drawing Sheets

MD
301
61
62
63
64
71
302
66
72
(a)
303
304
67
68
73
74
(b)
305
306
76
77
78
81(1)

SWEAT-ABSORBENT SHEET AND PROCESS FOR MAKING THE SAME

BACKGROUND OF THE INVENTION

The present invention relates to a sweat-absorbent sheet and more particularly to a sweat-absorbent sheet impregnated with antibacterial or bactericidal medicinal ingredient.

Sweat-absorbent sheets adapted to be used in disposable wearing articles such as disposable diapers, disposable training pants or disposable gowns are well known. For example, in the case of a disposable diaper disclosed in Japanese Unexamined Patent Application Publication No. 2000-189454 (REFERENCE 1), each of end flaps of the diaper is provided on its inner surface with an air-permeable sweat-absorbent sheet. In the case of the absorbent article disclosed in Japanese Unexamined Patent Application Publication No. 2004-358099 (REFERENCE 2), each of end flaps of the diaper is provided on its surface destined to come in contact with the user's skin with a sweat-absorbent sheet which is hydrophilic and air-permeable. These known sweat-absorbent sheets have been used to protect the users or the like from miliaria and/or contact dermatitis which would otherwise develop during use of such wearing articles. In the case of the absorbent articles disclosed in Japanese Unexamined Patent Application Publication No. 2001-299811 (REFERENCE 3) and Japanese Unexamined Patent Application Publication No. 2002-153507 (REFERENCE 4), a region of the articles facing the user's skin is coated with medicinal ingredient such as aloe extract to prevent development of contact dermatitis or the like.

While it may be possible for the sweat-absorbent sheets disclosed in REFERENCES 1, 2 to give the users feeling of coolness by absorbing sweat and to prevent development of contact dermatitis or the like, it will be difficult for these sweat-absorbent sheets to protect the users against contact dermatitis or the like when the user's perspiration is excessive. In the case of the absorbent articles disclosed in REFERENCES 3, 4, it may be possible to prevent development of contact dermatitis or the like under the effect of the medicinal ingredient but there is no feature found in these articles which can induce a feeling of coolness when the user becomes sweaty.

SUMMARY OF THE INVENTION

An object of the present invention is to provide a sweat-absorbent sheet adapted to give the user's sweaty skin feeling of coolness and at the same time adapted to prevent development of miliaria and/or contact dermatitis particularly when the sweat-absorbent sheet is used as a component of wearing articles such as disposable diapers.

According to first aspect of the present invention, there is provided a sweat-absorbent sheet and, according to second aspect of the present invention, a process for making the sweat-absorbent sheet. Details of these improvements will be described below.

The first aspect of the present invention relates to a sweat-absorbent sheet having hydrophilicity.

According to the first aspect of the present invention is as follows: A sweat-absorbent sheet has a first surface layer and a second surface layer lying on the opposite side of the first surface layer. Each of the first and second surface layers comprises a mixture layer of hydrophobic fibers as a main constituent made of a thermoplastic synthetic resin and hydrophilic fibers. The first and second surface layers sandwich therebetween an intermediate layer formed from the hydrophilic fibers, into which the hydrophobic fibers constituting at least one of the first and second surface layers extends. The hydrophobic fibers in the first and second surface layers is welded to crimped hydrophobic composite fibers mixed in the first surface layer, the second surface layer and the intermediate layer. The hydrophilic fibers are impregnated with medicinal ingredient and left behind on the hydrophilic fibers after the hydrophilic fibers have been dried.

In one preferred embodiment of the present invention according to the first aspect, the hydrophilic fibers are fibers selected from the group consisting of rayon, cotton and pulp fibers.

In another preferred embodiment of the present invention according to the first aspect, the rayon fibers are used to form the first surface layer and the second surface layer while the pulp fibers are used to form the intermediate layer.

In still another preferred embodiment of the present invention according to the first aspect, one or more quaternary ammonium salts selected as the medicinal ingredient from the group consisting of alkylpyridinium salt, alkyltrimethylammonium salt, alkylbenzylmethylammonium salt (benzalkonium chloride), dialkyldimethylammonium salt and benzethonium chloride is or are used as the medicinal ingredient.

In yet another preferred embodiment of the present invention according to the first aspect, the sweat-absorbent sheet constitutes at least apart of the surface of a disposable wearing article destined to come in contact with the user's skin.

In further another preferred embodiment of the present invention according to the first aspect, the disposable wearing article is a disposable diaper and the sweat-absorbent sheet is attached to the inner surface of the disposable diaper in its rear waist region.

The second aspect of the present invention relates to a process for making the sweat-absorbent sheet according to the first aspect of the present invention.

The improvement in the process for making the sweat-absorbent sheet according to the second aspect of the present invention for making the sweat-absorbent sheet comprises the steps of:

a. feeding a first web in a machine direction, the first web having a basis weight in a range of 7 to 20 g/m$^2$ and comprising first hydrophobic fibers made of thermoplastic synthetic resin constituting 60 to 80% by weight of the first web and first hydrophilic fibers selected from the group consisting of rayon, cotton and pulp fibers constituting 40 to 20% by weight of the first web;
b. feeding a second web in the machine direction and placing this second web on said first web, the second web having a basis weight in a range of 7 to 20 g/m$^2$ and comprising first hydrophilic fibers selected from the group consisting of rayon, cotton and pulp fibers;
c. feeding a third web in the machine direction and placing this third web on the second web, the third web having a basis weight in a range of 5 to 12 g/m$^2$ and comprising sheath/core type hydrophobic composite fibers consisting of polyethylene as the sheath and thermoplastic synthetic resin having a melting temperature higher than that of polyethylene as the core;
d. feeding a fourth web in the machine direction and placing this fourth web so as to obtain a first composite web comprising the first, second, third and fourth webs placed one on another, the fourth web having a basis weight in a range of 5 to 12 g/m$^2$ and comprising a mixture of second hydrophobic fibers made of thermoplastic synthetic resin constituting 60 to 80% by weight of the fourth web and third hydrophilic fibers selected from the group consisting of rayon, cotton and pulp fibers constituting 40 to 20% by weight of the fourth web;

e. subjecting the first composite web to treatment with columnar water jet of 10 to 100 kg/cm$^2$ targeting the first or fourth web to entangle component fibers of the first composite web together and thereby to obtain a second composite web;

f. drying the second composite web;

g. heating the second composite web up to a temperature at which polyethylene in the hydrophobic composite fibers is molten and welding the hydrophobic composite fibers to fibers being entangled with the hydrophobic composite fibers;

h. immersing the third composite web in aqueous solution of antibacterial or bactericidal medicinal ingredient to obtain a fourth composite web; and i. drying the fourth composite web impregnated with the aqueous solution to obtain the sweat-absorbent sheet.

In one preferred embodiment of the present invention according to the second aspect, a web having a basis weight in a range of 5 to 12 g/m$^2$ and comprising fourth hydrophilic fibers selected from the group consisting of rayon, cotton and pulp fibers constituting 0 to 50% by weight of this web and the composite fibers constituting 100 to 50% by weight of this web are used as the third web.

In another preferred embodiment of the present invention according to the second aspect, one or more quaternary ammonium salts may be selected from the group consisting of alkylpyridinium salt, alkyltrimethylammonium salt, alkylbenzylmethylammonium salt, dialkyldimethylammonium salt and benzethonium chloride is or are used as the medicinal ingredient.

The sweat-absorbent sheet according to the first aspect of the present invention is used in a manner that one of the first surface layer and the second surface layer is put in contact with the user's skin. While these two surface layers primarily comprise hydrophobic fibers, some amount of hydrophilic fibers contained therein absorbs sweat and then allows for permeation and spread of sweat toward the intermediate layer. Consequentially, sweat once having been absorbed can be spaced from the user's skin. The hydrophobic fibers constituting these two surface layers functions to prevent the amount of sweat retained in the intermediate layer from coming in contact with user's skin and thereby to maintain the user's skin dry so as to give the user's skin feeling of coolness. The hydrophilic fibers contained in this sweat-absorbent sheet are previously impregnated with antibacterial or bactericidal medicinal ingredient and dried so that the medicinal ingredient can stay behind on the sheet after the sheet has been dried. In this way, there is unlikely that proliferation of miliaria and/or contact dermatitis might be promoted due to the presence of sweat absorbed by the hydrophilic fibers.

According to the process for making the sweat-absorbent sheet as defined by the second aspect of the present invention, the first, second, third and fourth webs are placed one upon another to form the first composite web which is then subjected to the columnar water jet to obtain the second composite web, in which the component fibers of the respective fibrous webs are mechanically entangled together so that the first and second surface layers primarily comprising hydrophobic fibers are defined by the first web and the fourth web while the intermediate layer primarily comprising hydrophilic fibers is defined between these two surface layers. The composite fibers constituting the third web is also entangled with the fibers constituting the first, second and fourth webs and, at points of entanglement, the fibers are bonded together by means of polyethylene molten as the second composite web is heated. Thus the third composite web is obtained from the second composite web. The third composite web may be impregnated with aqueous solution of the medicinal ingredient and then dried to obtain the sweat-absorbent sheet containing the medicinal ingredient not on the hydrophobic fibers which is not easily wetted but primarily on the hydrophilic fibers.

Embodiments of the present invention according to its first and second aspects, respectively, and effect provided thereby will be described below.

DETAILED DESCRIPTION OF THE PREFERRED EMBODIMENTS

A sweat-absorbent sheet and a process for making the same according to the present invention will be more fully understood from the description given hereunder with reference to the accompanying drawings.

Figure 1:
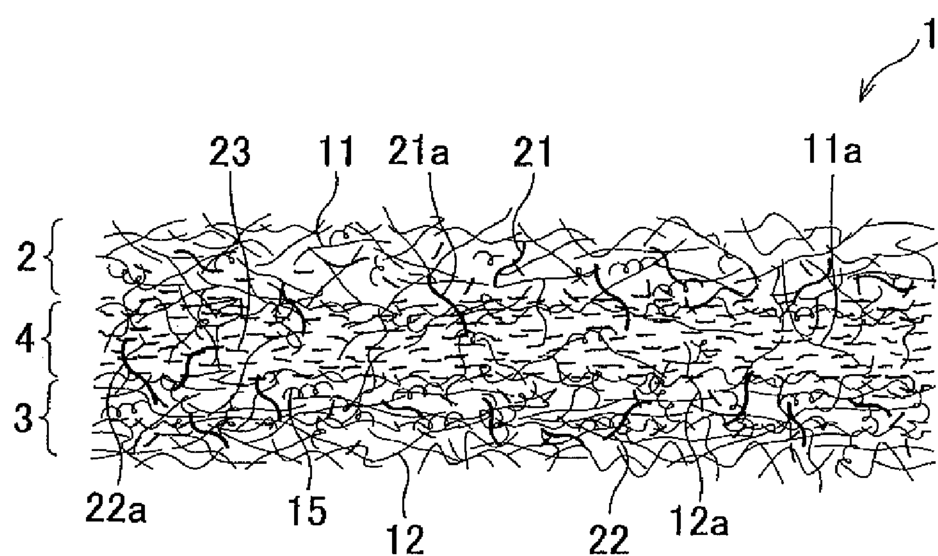
FIG. 1 is a sectional view of sweat-absorbent sheet.

FIG. 1 is a sectional view of a sweat-absorbent sheet 1. A sweat-absorbent sheet 1 comprises a top layer 2, a bottom layer 3 and an intermediate layer 4 sandwiched between these top and bottom layers 2, 3. The top layer 2 primarily comprises first hydrophobic fibers 11 and the bottom layer 3 primarily comprises second hydrophobic fibers 12, both made of thermoplastic synthetic resin. Both the first hydrophobic fibers 11 and the second hydrophobic fibers 12 are respectively mixed with first and second hydrophilic fibers 21, 22 which are present in relatively small quantity. The intermediate layer 4 primarily comprises third hydrophilic fibers 23 and sometimes the first and second hydrophobic fibers 11, 12 as well as the first and second hydrophilic fibers 21, 22 may extend into the intermediate layer 4. In FIG. 1, the first and second hydrophobic fibers extending into the intermediate layer 4 are designated by reference numerals 11*a*, 12*a*, respectively, and the first and second hydrophilic fibers extending into the intermediate layer 4 are designated by reference numerals 21*a*, 22*a*. Furthermore, crimped hydrophobic composite fibers 15 also is present in the top, bottom and intermediate layers 2, 3, 4 as well as in boundary zones thereof. These fibers 11, 12, 21, 22, 23 constituting the sweat-absorbent sheet 1 are mechanically entangled together and bonded to the composite fibers 15 at most points of these fibers 11, 12, 21, 22, 23 which are in contact with the composite fibers 15 as the composite fibers 15 is molten. It should be noted that the hydrophilic fibers are illustrated to be thicker than the hydrophobic fibers in order to distinguish the hydrophilic fibers from the hydrophobic fibers.

The first, second and third hydrophilic fibers 21, 22, 23 contain medicinal ingredient (not shown) impregnated on surfaces thereof having antibacterial or bactericidal activity on various bacteria which may proliferate and cause development of miliaria or contact dermatitis when the user's skin becomes sweaty. While at least the first and second hydrophobic fibers 11, 12 may contain the medicinal ingredient impregnated on the surfaces thereof, the preferred sweat-absorbent sheet 1 contains the medicinal ingredient distributed on almost all of the first, second and third hydrophilic fibers 21, 22, 23.

In the case of the seat-absorbent sheet 1 constructed in the manner as has been described above, when the top layer 2 is put in contact with the user's skin, such amount of sweat can be absorbed by the first hydrophilic fibers 21 constituting the top layer 2. Sweat seeps and spreads in the intermediate layer 4 and is retained by the third hydrophilic fibers 23. Sweat retained in this manner is prevented by the presence of the first hydrophobic fibers 11 in the top layer 2 from coming in contact with user's skin. Consequentially, the user experiences feeling of coolness rather than feeling of dampness. The third hydrophilic fibers 23 having absorbed sweat contains medicinal ingredient impregnated on the surface thereof and proliferation of *Staphylococcus epidermidis* as well as miliaria due to the presence of such sweat can be inhibited by the medicinal ingredient. As the medicinal ingredient, one or more quaternary ammonium salts may be selected from the group consisting of alkylpyridinium salt, alkyltrimethylammonium salt, alkylbenzylmethylammonium salt (benzalkonium chloride), dialkyldimethylammonium salt and benzethonium chloride. The medicinal ingredient may be mixed, if desired, with the other substance such as catechin.

The first hydrophobic fibers 11 constituting the top layer 2 in the sweat-absorbent sheet 1 is made of thermoplastic synthetic resin such as polyester, polypropylene or nylon, preferably having a melting point higher than that of polyethylene, a fibers-length of at least 30 mm and fineness in a range of 0.1 to 5 dtex. The first hydrophilic fibers constituting the top layer 2 is made of hydrophilic fibers such as rayon, cotton, preferably having a fibers-length of at least 30 mm. The second hydrophobic fibers 12 as well as the second hydrophobic fibers 22 constituting the bottom layer 3 may be made of the same materials as those used to form the top layer 2. However, it is not essential to make the top layer 2 from same fibers as those for the bottom layer 3. The third hydrophilic fibers 23 forming the intermediate layer 4 is hydrophilic fibers such as rayon, cotton or pulp fibers. The intermediate layer 4 is sandwiched between the top and bottom layers 2, 3 and therefore it is unlikely that the fibers forming the intermediate layer 4 might fall off from the sweat-absorbent sheet 1 even if the fibers forming this layer 4 has a fibers-length of 5 mm or less. Thus the present invention allows a manufacturing cost for the sweat-absorbent sheet 1 to be reduced by using pulp fibers having a unit price lower than a unit price of rayon fibers. The crimped composite fibers 15 contained in the respective layers of the sweat-absorbent sheet 1 may comprise, for example, polyethylene as its sheath and polypropylene as its core, used by a ratio of 5 to 20% by weight with respect to a total weight of the sweat-absorbent sheet 1. Sheath component of the composite fibers 15 made of polyethylene is welded to points along the first hydrophobic fibers 11 as well as the second hydrophobic fibers being in contact with the sheath component. In this way, the composite fibers 15 functions to maintain the desired shape of the sweat-absorbent sheet 1 constant before and after absorption of sweat. Specifically, in the sweat-absorbent sheet 1 before absorption of sweat, i.e., during a period elapsing from production to actual use of the sweat-absorbent sheet 1 , the composite fibers 15 well prevents the construction of the sheet from falling apart and, in addition, prevents the sheet from fluffing. In the sweat-absorbent sheet 1 after absorption of sweat, the composite fibers 15 well restrains undesirable change in respective volumes of the first, second and third hydrophilic fibers 21, 22, 23 which would otherwise occur due to absorption of sweat. The composite fibers 15 functions thereby to maintain a thickness of the sweat-absorbent sheet 1 substantially constant and to prevent a construction of the sweat-absorbent sheet 1 from coming apart. Should the construction of the sweat-absorbent sheet 1 come apart as a result of sweat absorption, it would be likely that the third hydrophilic fibers 23 in wet condition might undesirably come in contact with the user's skin.

Figure 2:
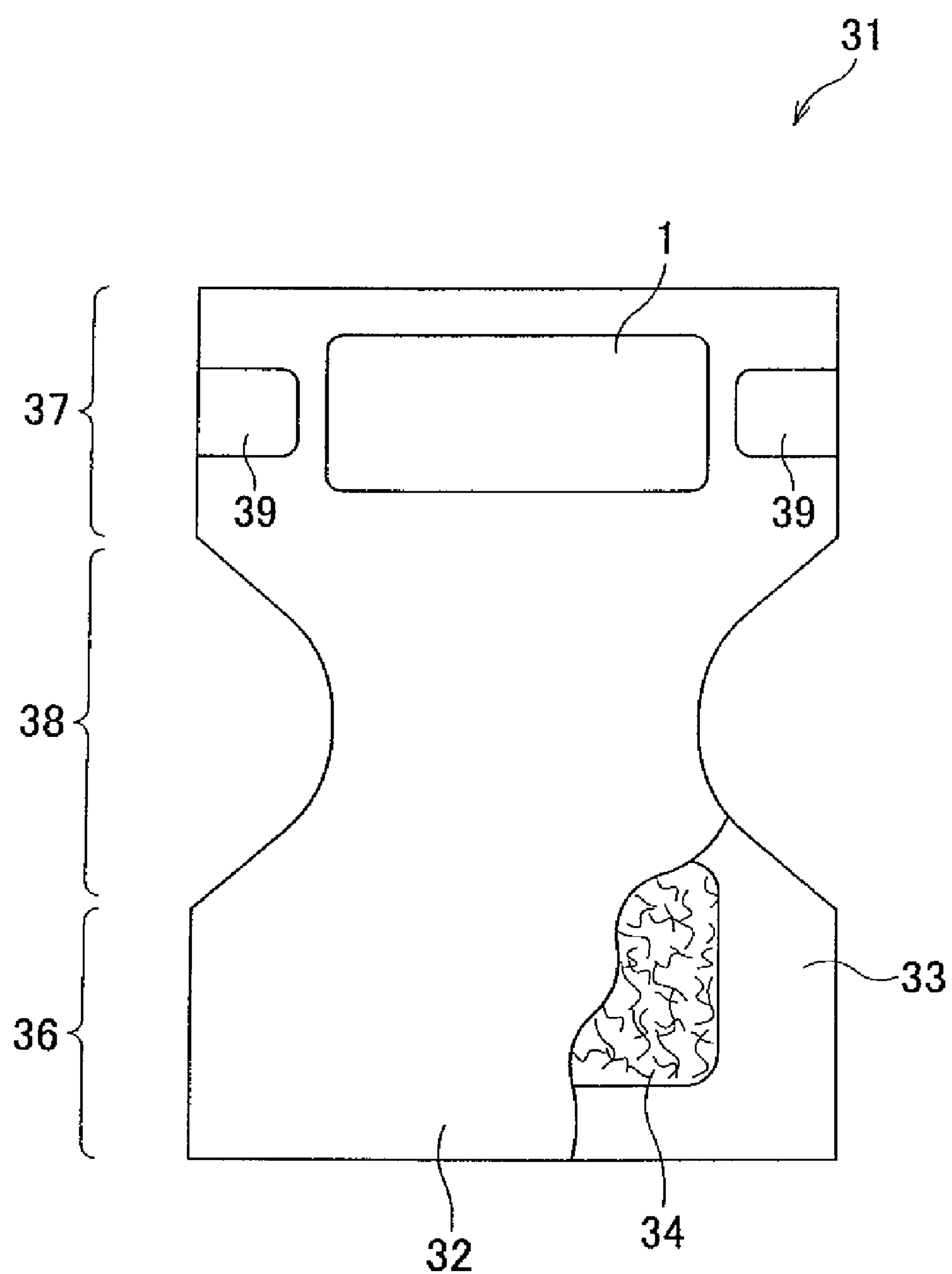
FIG. 2 is a partially cutaway plan view of disposable diaper.

FIG. 2 is a partially cutaway plan view of a disposable diaper 31. The diaper 31 comprises a liquid-pervious topsheet 32, a liquid-impervious backsheet 33 and a liquid-absorbent core 34 sandwiched between these two sheets 32, 33 and wrapped with a tissue paper. The diaper 31 has a front waist region 36, a rear waist region 37 and a crotch region 38 cooperating together to cover the user's body. The rear waist region 37 is provided on its transversely opposite side edges with fasteners 39, 39 used to connect the front and rear waist regions 36, 37 together. In the rear waist region 37, the diaper 31 is provided on the topsheet 32 with a rectangular strip of the sweat-absorbent sheet 1, as seen in FIG. 1, attached to an appropriate zone of the topsheet 32 by means of adhesive or suitable welding technique. The sweat-absorbent sheet 1 reliably absorbs an amount of sweat in the user's lumber region so that the user of this diaper 31 may experience a feeling of coolness and, at the same time, be protected against suffering from miliaria. The sweat-absorbent sheet 1 according to the present invention is not limited to the application as illustrated but may be used also as pillow-covers or lining clothes of wearing articles such as medical gowns.

The inventors measured amount of sweat on lumber regions of 3 two years old infants having spent 3 hours in a room at 33±1° C. and 75±5% RH by using perspiration meter SKD-1000 available from SKINOS CO., LTD. (Nagoya, Aichi, Japan) and obtained an average amount of 192 $g/m^2 \cdot hr$. Taking account of a fact that the infant from two to three years old usually continues to wear a disposable diaper for approximately 3 hours before exchange of this diaper, the inventors estimated that the sweat-absorbent sheet 1 preferably achieves a sweat-absorbing capacity corresponding to at least [average amount of perspiration per $m^2$ hr]×3, i.e., in a range of 550 to 570 $g/m^2 \cdot hr$. Based on such estimation, the inventors selected the respective component fibers shown in FIG. 1, specifically, polyester fibers having a basis weight of 8.4 $g/m^2$ as the first hydrophobic fibers 11, polyester fibers having a basis weight of 4.9 $g/m^2$ as the second hydrophobic fibers 12, rayon fibers having a basis weight of 3.6 $g/m^2$ as the first hydrophilic fibers 21, rayon fibers having a basis weight of 4.9 $g/m^2$ as the second hydrophilic fibers 22, pulp fibers having a basis weight of 12 $g/m^2$ as the third hydrophilic fibers 23, and polypropylene (core)/polyethylene (sheath) composite fibers having a basis weight of 4.2 $g/m^2$ as the composite fibers 15. These component fibers were combined together to obtain web having a basis weight of 38 $g/m^2$. This web was then impregnated with cetylpyridinium chloride and catechin to obtain the sweat-absorbent sheet 1 having a thickness of 0.5 mm. After immersed in water for 3 minutes and then left dry for 5 minutes, amount of water absorption was approximately 705 $g/m^2$. The inventors evaluated such amount of sweat absorption per unit area ($m^2$) of the user's skin to be acceptable even when the sheet is used as the important component in the diaper 31 adapted to be put on the user's body for 3 hours or longer. Actually, this sweat-absorbent sheet 1 dimensioned in approximately 55×285 mm was attached to the diaper 31 for infant and this diaper 31 was put on the body of 2 years old infant. The test result indicated that no sweat was found in the region of the infant's skin occupied by the sweat-absorbent sheet 1.

Figure 3:
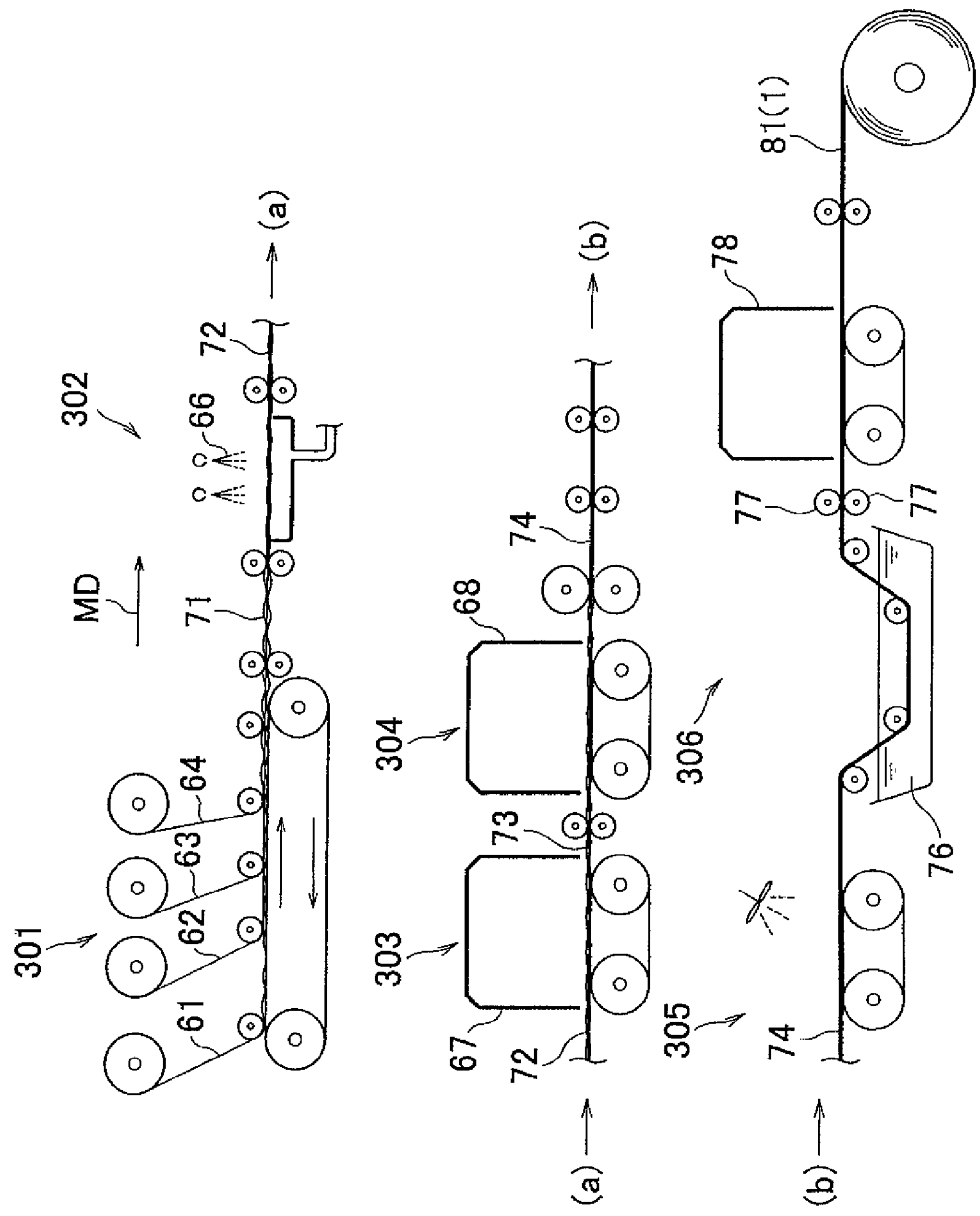
FIG. 3 is a diagram illustrating a process for making sweat-absorbent sheet.

FIG. 3 is a diagram illustrating a process for making the sweat-absorbent sheet 1. In a first step 301, first web 61 having a basis weight in a range of 7 to 20 $g/m^2$ is fed in a machine direction MD from the left as viewed in the diagram.

The first web 61 comprises a mixture of first hydrophobic fibers made of thermoplastic synthetic resin constituting 60 to 80% by weight of the mixture and first hydrophilic fibers made of any one of rayon, cotton and pulp fibers constituting 40 to 20% by weight of the mixture. Then second web 62 having a basis weight in a range of 7 to 20 g/m$^2$ and comprising second hydrophilic fibers selected from the group consisting of rayon, cotton and pulp are fed in the machine direction MD so as to be placed on the first web 61. Then third web 63 having a basis weight in a range of 5 to 12 g/m$^2$ is fed in the machine direction MD so as to be placed on the second web 62. The third web 63 comprises sheath/core type hydrophobic composite fibers consisting of polyethylene as the sheath and thermoplastic synthetic resin having a melting temperature higher than that of polyethylene, e.g., polypropylene. Then fourth web 64 having a basis weight in a range of 5 to 12 g/m$^2$ comprising a mixture of second hydrophobic fibers made of thermoplastic synthetic resin constituting 60 to 80% by weight and third hydrophilic fibers selected from the group consisting of rayon, cotton and pulp fibers constituting 40 to 20% by weight is fed in the machine direction so as to be placed on the third web 63. In this way, a first composite web 71 comprising the first, second, third and fourth webs 61, 62, 63, 64 placed one on another is obtained. It is possible without departing from the scope of the invention to form the third web 63 by web having a basis weight in a range of 5 to 12 g/m$^2$ comprising hydrophobic composite fibers mixed with fourth hydrophilic fibers selected from the group consisting of rayon, cotton and pulp fibers of up to 50% by weight.

In a second step 302, the first composite web 71 is subjected to treatment with columnar water jet 66 of 10 to 100 kg/cm$^2$ targeting the first web 61 and/or the fourth web 64 to entangle the component fibers of the first composite web 71 together and thereby to obtain a second composite web 72. FIG. 3 exemplarily illustrates the columnar water jet 66 targeting the fourth web 64.

In a third step 303, the second composite web 72 is guided to a first heating oven 67 in which the web 72 is dried under hot blast at an appropriate temperature, for example, at a temperature in a range of 60 to 90° C. and thereby a third composite web 73 is obtained.

In a fourth step 304, the third composite web 73 dried in the precedent step is guided to a second heating oven 68 in which the sheath/core type composite fibers constituting the third web 73 is crimped and, at the same time, polyethylene as the sheath component is molten under hot blast at a temperature of approximately 130° C. so that the composite fibers may be bonded to the fibers being entangled therewith to obtain a fourth composite web 74.

In a fifth step 305, the fourth composite web 74 having left the second heating oven 68 is cooled.

In a sixth step 306, the fourth composite web 74 is immersed in aqueous solution of antibiotic or bactericidal medicinal ingredient, then squeezed by a pair of nip rolls 77 and guided to a third heating oven 78 in which the fourth composite web 74 is dried at a temperature in a range of 100 to 140° C. The fourth composite web 74 dried in this manner is taken up in the form of continuum 81 of the sweat-absorbent sheet 1. In the fourth composite web 74, the first and second hydrophobic fibers as well as the composite fibers are not easily wetted with the aqueous solution of medicinal ingredient while the first, second and third hydrophilic fibers are easily wetted with this aqueous solution. Consequentially, the medicinal ingredient stays behind primarily on these first, second and third hydrophilic fibers in the continuum 81.

The continuum 81 is cut into an appropriate shape to obtain the individual sweat-absorbent sheet 1 as shown in FIG. 1.

The first hydrophobic fibers and the first hydrophilic fibers constituting the first web 61 used to obtain the continuum 81 are destined to become the first hydrophobic fibers 11 and the first hydrophilic fibers 21 in the sweat-absorbent sheet 1, respectively. The second hydrophilic fibers in the second web 62 are destined to become the third hydrophilic fibers 23 in the sweat-absorbent sheet 1. The composite fibers in the third web 63 are destined to become the composite fibers 15 in the sweat-absorbent sheet 1. The second hydrophobic fibers and the third hydrophilic fibers in the fourth web 64 are destined to become the second hydrophobic fibers 12 and the second hydrophilic fibers 22, respectively. If the third web 63 includes the fourth hydrophilic fibers, this fourth hydrophilic fibers are destined to become a part of the first, second or third hydrophilic fibers 21 22, 23 in the sweat-absorbent sheet 1.

The manner in which the sweat-absorbent sheet 1 is impregnated with the medicinal ingredient is not limited to the manner as illustrated. For example, it is possible to impregnate the fourth composite web 74 with the medicinal ingredient by spraying or roll-coating the aqueous solution of medicinal ingredient and then to dry this fourth composite web 74.

Both the upper surface layer 2 and the lower surface layer 3 of the sweat-absorbent sheet 1 obtained by the process as illustrated are substantially not impregnated with the medicinal ingredient and therefore this sweat-absorbent sheet 1 can be used for the infant whose skin is sensitive to the medicinal ingredient. In the second step 302, the first composite web 71 may be subjected to the columnar water jet in order to force the first hydrophobic fibers contained in the first web 61 as well as the second hydrophobic fibers contained in the fourth web 64 to extend into the second web 62 and simultaneously to force these first and second hydrophobic fibers to be entangled with the composite fibers.

In the process of FIG. 3, a card web having a basis weight of 12 g/m$^2$ comprising polyester fibers (fibers-length: about 44 mm) having a fineness of 1.7 dtex constituting 70% by weight of the card web and rayon fibers (fibers-length: about 44 mm) having a fineness of 1.25 dtex constituting 30% by weight of the card web was used as the first web. A card web having a basis weight of 12 g/m$^2$ comprising pulp fibers constituting 100% by weight of this card web was used as the second web. A card web having a basis weight of 7 g/m$^2$ comprising rayon fibers (fibers-length: about 50 mm) having a fineness of 1 dtex constituting 40% by weight of this card web and polyethylene (sheath)/polypropylene (core) composite fibers (fibers-length: about 45 mm) having a fineness of 2.0 dtex constituting 60% by weight of this card web was used as the third web. Card web having a basis weight of 7 g/m$^2$ comprising polyester fibers (fibers-length: about 50 mm) having a fineness of 1 dtex constituting 70% by weight and rayon fibers (fibers-length: about 50 mm) having a fineness of 1 dtex constituting 30% by weight was used as the fourth web. The first composite web corresponding to laminate of these first, second, third and fourth webs was subjected to columnar water jet of 40 to 80 kg/cm$^2$ targeting the first web and then targeting the fourth web.

After the second composite web had been dried under hot blast at a temperature of 80° C. and thereby the third composite web had been obtained, this third composite web was subjected to hot blast at a temperature of 130° C. Under the effect of such hot blast, the composite fibers constituting the third web is crimped while polyethylene as the sheath component of the composite fibers was molten so as to bond the composite fibers to the fibers being entangled with the composite fibers and thereby the fourth composite web was obtained.

The fourth composite web was immersed in aqueous solution containing 0.1620 g/l of cetylpyridinium chloride and 0.0810 g/l of catechin, then squeezed by the nip rolls for draining and then dried under hot blast at a temperature in a range of 100 to 140° C. for a time in a range of 0.5 to 3 minutes. As a result, the continuum of sweat-absorbent sheet having a basis weight of about 38 g/m$^2$ and a thickness of about 0.5 mm was obtained, in which the medicinal ingredient stayed behind primarily on the pulp fibers and the rayon fibers.

TABLE 1 indicates a result of observation concerning the effect of the sweat-absorbent sheet according to the embodiment as has been described just above. Specifically, pillows wrapped with the sweat-absorbent sheets obtained according to the above-described embodiment, respectively, were used for ten 24 to 36 months old infants (panels A to J) for 5 days and development of miliaria on neck line of each infant was observed. As Comparative Example, a spun lace nonwoven fabric having a basis weight of about 38 g/m$^2$ and a thickness of about 0.5 mm comprising polyester fibers (fibers-length: about 50 mm) having a fineness of 1 dtex constituting 70% by weight of this nonwoven fabric and rayon fibers (fibers-length: about 50 mm) having a fineness of 1 dtex constituting 30% by weight of this nonwoven fabric was used also for similar ten infants. In TABLES 1 and 2, the degree of miliaria development was evaluated depending on the number of individual miliaria spots.

TABLE 1

| Panel | Example (Sweat-absorbent sheet) Miliaria | Comparative Example (Span lace nonwoven fabric) Miliaria |
|---|---|---|
| A | – | + |
| B | – | 2+ |
| C | – | + |
| D | – | – |
| E | – | – |
| F | – | + |
| G | – | 3+ |
| H | – | 2+ |
| I | – | – |
| J | – | + |

TABLE 2

| Miliaria | Classified determination |
|---|---|
| Unchanged | – |
| 1 to 3 miliaria spots | + |
| 4 to 9 miliaria spots | 2+ |
| 10 or more miliaria spots | 3+ |

The present invention makes it possible to manufacture the sweat-absorbent sheet adapted to provide the user with feeling of coolness and to prevent miliaria from developing on the user's skin.

The entire discloses of Japanese Patent Application Nos. 2005-380298 filed on Dec. 28, 2005 and 2006-109897 filed on Apr. 12, 2006, respectively, including specification, drawings and abstract are herein incorporated by reference in their entirety.

What is claimed is:

1. A sweat-absorbent sheet, comprising:

a first surface layer and a second surface layer opposite to said first surface layer, each of said first and second surface layers comprising a mixture of first and second hydrophobic fibers of thermoplastic synthetic resin and first and second hydrophilic fibers, respectively;

an intermediate layer sandwiched between the first and second surface layers and including third hydrophilic fibers, wherein at least one of said first and second hydrophobic fibers extends into the intermediate layer, said first and second hydrophobic fibers in said first and second surface layers are welded to crimped hydrophobic composite fibers mixed in said first surface layer, said second surface layer and said intermediate layer, and said first, second and third hydrophilic fibers are impregnated with medicinal ingredient.

2. The sweat-absorbent sheet defined by claim 1, wherein said first, second and third hydrophilic fibers are fibers selected from the group consisting of rayon, cotton and pulp fibers.

3. The sweat-absorbent sheet defined by claim 1, wherein said first surface layer and said second surface layer comprise rayon fibers while said intermediate layer comprises pulp fibers.

4. The sweat-absorbent sheet defined by claim 1, wherein, as the medicinal ingredient, one or more quaternary ammonium salts are selected from the group consisting of alkylpyridinium salt, alkyltrimethylammonium salt, alkylbenzylmethylammonium salt (benzalkonium chloride), dialkyldimethylammonium salt and benzethonium chloride.

5. The sweat-absorbent sheet defined by claim 1, wherein said sweat-absorbent sheet constitutes at least a part of the surface of a disposable wearing article destined to come in contact with a user's skin.

6. The sweat-absorbent sheet defined by claim 5, wherein said disposable wearing article is a disposable diaper and said sweat-absorbent sheet is attached to an inner surface of said disposable diaper in its rear waist region.

7. The sweat absorbent sheet defined by claim 1, wherein said first and second hydrophobic fibers, said first, second and third hydrophilic fibers and said hydrophobic composite fibers are mechanically entangled together.

8. The sweat absorbent sheet defined by claim 1, wherein respective quantities of said first and second hydrophilic fibers in said first and second surface layers are less than those of said first and second hydrophobic fibers in said first and second surface layers.

9. A sweat absorbent sheet which comprises:

a first surface layer;

a second surface layer;

an intermediate layer sandwiched between said first and second surface layers;

said first surface layer comprising first hydrophobic fibers of thermoplastic synthetic resin having a melt temperature higher than that of polyethylene, and first hydrophilic fibers mixed with said first hydrophobic fibers, wherein a quantity of said first hydrophilic fibers is less than that of said first hydrophobic fibers;

said second surface layer comprising second hydrophobic fibers of thermoplastic synthetic resin having a melt temperature higher than that of polyethylene, and second hydrophilic fibers mixed with said second hydrophobic fibers, wherein a quantity of said second hydrophilic fibers is less than that of said second hydrophobic fibers;

said intermediate layer comprising third hydrophilic fibers;

sheath/core type crimped hydrophobic composite fibers of polyethylene as said sheath and thermoplastic synthetic resin having a melt temperature higher than that of polyethylene as said core, being mixed with said first and second hydrophobic fibers, said first, second and third hydrophilic fibers, and said hydrophobic composite fibers;

parts of said first and second hydrophobic fibers and said first and second hydrophilic fibers in said first and second surface layers extend into said intermediate layer; and said first and second hydrophobic fibers, said first and second hydrophilic fibers and said hydrophobic composite fibers being mechanically entangled together, wherein said sheath of said hydrophobic composite fibers are welded to said first and second hydrophobic fibers; and said first, second and third hydrophilic fibers being impregnated with medicinal ingredient.

10. The sweat-absorbent sheet defined by claim 9, wherein, the medicinal ingredient includes one or more quaternary ammonium salts selected from the group consisting of alkylpyridinium salt, alkyltrimethylammonium salt, alkylbenzylmethylammonium salt (benzalkonium chloride), dialkyldimethylammonium salt and benzethonium chloride.

* * * * *